United States Patent [19]
Lukosz

[11] Patent Number: 5,120,131
[45] Date of Patent: Jun. 9, 1992

[54] METHOD AND APPARATUS FOR SELECTING DETECTION OF CHANGES IN SAMPLES BY INTEGRATED OPTICAL INTERFERENCE

[76] Inventor: Walter Lukosz, Burstwiesenstr. 55, Greifensee, Switzerland, 8606

[21] Appl. No.: 573,190
[22] PCT Filed: Feb. 14, 1988
[86] PCT No.: PCT/EP88/00108
§ 371 Date: Aug. 10, 1990
§ 102(e) Date: Aug. 10, 1990
[87] PCT Pub. No.: WO89/07756
PCT Pub. Date: Aug. 24, 1989
[51] Int. Cl.⁵ .............................. G01B 9/02
[52] U.S. Cl. .................. 356/351; 356/345; 356/361; 385/12
[58] Field of Search ........ 356/345, 351, 361, 128, 356/133, 136, 246; 350/96.12, 96.15; 250/227.17, 227.19, 227.27

[56] References Cited
U.S. PATENT DOCUMENTS
4,932,783 6/1990 Kersey et al. .............. 356/345
4,940,328 7/1990 Hartman ................... 350/96.12
4,950,074 8/1990 Fabricius .................. 356/361

FOREIGN PATENT DOCUMENTS
3723159 1/1988 Fed. Rep. of Germany .
2156970 10/1985 United Kingdom .

OTHER PUBLICATIONS
"Polarization Fluctuations in Optical Fibers Based on Probability", Imai et al., Optics Letters, Sep. 1987, pp. 723–725.

Primary Examiner—Samuel A. Turner
Attorney, Agent, or Firm—McAulay Fisher Nissen Goldberg & Kiel

[57] ABSTRACT

In an integrated optical interference method, polarized laser light is incoupled into a planar waveguide, propagates in the waveguide as a guided wave, which consists of two mutually coherent, orthogonally polarized modes, interacts at least once with the sample, which is applied to the surface of a section of the waveguide called measuring section, and subsequently is outcoupled out of the waveguide. The time dependent phase difference $\Delta\Phi(t)$ between the two orthogonal polarization components of the outcoupled light is measured with a device comprising photodetectors and polarization optical components.

23 Claims, 3 Drawing Sheets

METHOD AND APPARATUS FOR SELECTING DETECTION OF CHANGES IN SAMPLES BY INTEGRATED OPTICAL INTERFERENCE

BACKGROUND OF THE INVENTION

The present invention relates to an integrated optical interference method according to the preamble of claim 1.

Optical film waveguides consist of a thin waveguiding film of higher refractive index on a substrate of lower refractive index. Strip waveguides consist of a strip of higher refractive index on a substrate of lower refractive index or inlaid into the surface of said substrate. Also the superstrate with which the film or strip waveguide is covered has to have a lower refractive index than the film or strip waveguide. According to geometrical optics the optical waves are guided in film waveguides by total internal reflection in the plane of the film; in strip waveguides they are additionally also guided transversally. An important special case of the film waveguide is the planar waveguide where the substrate is planar.

According to wave optical or electrodynamical theory, optical waves propagate in waveguides in the form of guided modes which are characterized by their frequency $\nu$ or their vacuum-wavelength $\lambda = c/\nu$, their polarization, their transverse field distribution, and their phase velocity $v_p = c/N$. Here c is the velocity of light in vacuum and N the effective refractive index of the mode. In planar waveguides the modes are designated according to their polarization as $TE_m$-(transverse electric) and $TM_m$-(transverse magnetic) modes. The mode number $m = 0, 1, 2, \ldots$ denotes modes with different transverse field distributions. Also in strip waveguides, modes with different polarizations and transverse field distributions can propagate. The effective refractive indices N depend on the frequency $\nu$, the polarization, the mode number, and the properties of the waveguide, such as the refractive indices of the substrate, the superstrate, and the waveguiding film or strip, and the latters thickness and thickness and width, respectively. Light of the same frequency $\nu$ can propagate in a waveguide simultaneously in the form of modes of different polarization, for example, in a planar waveguide as $TE_m$- and as $TM_M$-modes with the same mode number $m = 0, 1, \ldots$. The effective refractive indices $N(TE_m)$ and $N(TM_M)$ differ from each other.

In integrated optical two beam interferometers according to the prior state of the art, as the Michelson- or Mach-Zehnder-interferometer, a guided wave or mode is with a beam splitter divided up into two partial waves 1 and 2, which propagate along different paths and are superimposed by a beam recombiner. Beam splitter and recombiner can in planar waveguides be realized, for example, by gratings, and in the case of strip waveguides by 3dB-couplers. The partial waves 1 and 2 interfere with the phase difference $\phi_1 - \phi_2 = (2\pi/\lambda)[\int_1 N\, ds - \int_2 N\, ds]$, where the integral $\int_j N\, ds$ with the incremental path element ds is the path integral over the effective refractive index N on the path of the partial wave $j = 1, 2$ and the expression in the bracket is the optical path difference. The intensity at the output port of the interferometer is $$I = I_1 + I_2 + 2(I_1 I_2)^{\frac{1}{2}} \cos(\phi_1 - \phi_2). \tag{1}$$

The intensity can be measured photoelectrically. By counting the interference fringes, i.e., the maxima and minima of the intensity I, the values of the phase difference $\phi_1 - \phi_2$ can be determined as integers of $2\pi$ and of $\pi$, respectively.

With an integrated optical interferometer according to the prior state of the art changes of the effective refractive index N can be measured, if either the geometrical path lengths in the two legs of the interferometer are chosen to be of different lengths, or if N is changed in one leg only but remains constant in the other leg. Integrated optical interferometers according to the prior state of the art have the disadvantage of being expensive; their fabrication is complicated since microstructures have to be very precisely produced.

The object of the present invention is to provide an integrated optical interference method for the selective detection of substances in liquid or gaseous samples, and/or for the measurement of changes of the refractive indices of liquid or gaseous samples, and/or of the concentrations of ions, which in spite of its high sensitivity and large measurement range can be realized more easily and cheaply, and requires no waveguides with structures, such as beam splitters, gratings, 3dB-couplers, etc., but only needs a single planar waveguide or a single strip waveguide, and to provide an apparatus which can be directly inserted into the sample to be analysed.

The method and apparatus of the present invention solves the above described problem.

In a planar waveguide the two orthogonally polarized modes are a $TE_m$-mode and a $TM_{m'}$-mode, where the mode numbers m and m' are either identical or different; preferably the two modes are the $TE_0$-mode and the $TM_0$-mode. The laser light is most easily incoupled into the waveguide through its front face. Also the outcoupling is done most easily through the end or front faces. The incident laser light either has to be linearly polarized under an angle $\psi$ with respect to the normal on the waveguide, where $\psi \neq 0°$ and $\neq 90°$ and preferably is $\psi = 45°$, or it has to be elliptically, preferably circularly, polarized. The outcoupled laser light has two mutually orthogonal polarization components s and p, where the p component, which is linearly polarized in direction of the normal on the waveguide, is generated by the TM-mode, and the s component, which is polarized parallel to the plane of the film, is generated by the TE-mode.

The sample is applied to the surface of the waveguide, at least in a waveguide section called measuring section, and if the surface is coated with a chemically selective sensitive layer, which is called chemo-responsive layer in the following, the sample is applied to this chemo-responsive layer; or a part of the waveguide with the measuring section is inserted into the sample.

The light of the two orthogonal polarization components s and p in the outcoupled light is mutually coherent; between the two components a phase difference $\Delta\Phi(t)$ exists which depends on time t if a time dependent change occurs in the sample or when the sample is applied to the measuring section. The phase difference $\Delta\Phi(t)$ is measured as a function of time t and therefrom the change of the quantity to be measured is inferred or quantitatively determined. Several particularly suitable methods for the measurement of $\Delta\Phi(t)$ are described below.

For the method according to the present invention the following points are essential:

In light propagation through non-birefringent media, such as air or optical elements, such as lenses, the optical paths lengths, i.e., the path integrals over the local refractive index times the incremental path element, are equal for the two orthogonal polarization components. The phase difference between the two polarization components is not changed during their propagation. In the method according to the present invention, this result holds for the light propagation before the waveguide and after the waveguide, i.e., for the paths between the laser and the waveguide and between the waveguide and the photodetector, respectively. Consequently, the phase difference $\Delta\Phi(t)$ between the two polarization components is the same everywhere in the outcoupled light. Therefore the interferometer is insensitive against vibrations and temperature changes, which cause optical path length changes. This property is very advantageous because the mechanical construction of the interferometer does not need to have the great stability which some other interferometers in threedimensional optics require.

With polarization optical components, such as phase retardation plates, for example $\lambda/4$-plates, and/or beam splitters, additional phase differences $\Phi_0$ between the polarization components can be produced. Such phase differences $\Phi_0$ which are introduced for the purpose of measuring the phase difference $\Delta\Phi(t)$ will be considered in more detail below.

It is very surprising that during the light propagation in the waveguide a phase difference $\Delta\Phi(t)$ between the two mutually orthogonal polarized modes arises due to the interaction with the sample. This phase difference $\Delta\Phi(t)$ depends on time, if a temporal changes occur in the sample or if the sample is applied to the measuring section. The existence of the phase difference $\Delta\Phi(t)$ can be understood in the following way: the light of the modes is guided by total internal reflection in the waveguiding film or strip; however, the field distribution reaches out—in the form of an evanescent wave—into the superstrate, i.e., into the chemo-responsive layer and/or into the sample. The penetration depths of the evanescent fields of the two orthogonally polarized modes are different and, consequently, also the strength of their interaction with the sample.

Quantitatively, this behaviour can be described with the effective refractive indices of the two orthogonally polarized modes, what is explained in more detail for the $TE_0$- and the $TM_0$-modes of planar waveguides. The effective refractive indices $N(TE_0)$ and $N(TM_0)$ of the two modes are different. Also the effective index changes $\Delta N(TE_0)$ and $\Delta N(TM_0)$ which arise due to interaction of the modes with the sample are different. Surprisingly it was found, that the difference $\Delta N \equiv \Delta N(TE_0) - \Delta N(TM_0)$ can assume rather large values, for example, 30-50% of the value of $\Delta N(TE_0)$ itself.

During propagation of the measuring section of length L the phase of a mode is changed by $$\Delta\Phi(L) - \Delta\Phi(0) = 2\pi(L/\lambda)N. \tag{2}$$

For the phase difference $\Delta\Phi(L)$ of the two modes at the end of the measuring section it follows from Eq. (2)

$$\Delta\Phi(L) = 2\pi(L/\pi)[N(TE_0) - N(TM_0)] + \Delta\Phi(0), \tag{3}$$

where $\Delta\Phi(0)$ is their phase difference at the beginning of the measuring section. If the effective refractive indices change as functions of time t, viz., $N(TE_0)$ by $\Delta N(t;TE_0)$ and $N(TM_0)$ by $\Delta N(t;TM_0)$, the phase difference $\Delta\Phi(L)$ changes with time by $$\Delta\Phi(t) = 2\pi(L/\lambda)\Delta N(t), \tag{4}$$

where $$\Delta N(t) = \Delta N(t;TE_0) - N(t;TM_0). \tag{5}$$

The reasons why the effective refractive indices and, consequently, the phase difference $\Delta\Phi(t)$ change with time when the sample changes temporally or is applied to the measuring section will be explained below.

In the case of the planar waveguide, the $TE_0$-mode coupled out of the waveguide generates the polarization component s, and the outcoupled $TM_0$-mode the polarization component p. Between said two polarization components s and p the phase difference is $\Delta\Phi(t) + \Delta\Phi$, where $\Delta\Phi$ is constant. The phase difference $\Delta\Phi(t)$ can be measured with several different methods. Common to all those methods is that the two mutually orthogonally polarized components in the outcoupled light, are superimposed by a polarizer or another polarizing optical component so that they can interfere with each other, and that the resulting intensities $I_j(t)$ are measured in one or several measurements channels $j = 1, \ldots, M$ with (M = 1,2,3 or 4). If only a single measurement channel is used, the outcoupled light falls through a polarizer onto a photodetector. The transmission direction of the polarizer is orientated to coincide with the bisector of the directions of polarization of the linearly polarized components s and p. The intensity measured by the photodetector is $$I = I_s + I_p + 2(I_s I_p)^{\frac{1}{2}} \cos[\Delta\Phi + \Delta\Phi(t)], \tag{6}$$

where $I_s$ and $I_p$ are the intensities that the polarization components s and p would produce separately, $\Delta\Phi$ is the constant phase difference, and $\Delta\Phi(t)$ is the time dependent phase difference arising from the temporal changes of the quantity to be measured. If maxima and minima of $I(t)$ are counted, then $\Delta\Phi(t)$ can be measured with a resolution of $\delta(\Delta\Phi) = \pi$. Preferable $I_s = I_p$ is chosen, for maximum contrast of the interference fringes.

The sensitivity of the method according to the present invention is proportional to the length L of the measuring section. An advantage is that the length L can be chosen in a wide range, for example, from a few millimeters to a few centimeters. For a length of the measuring section of, for instance, L = 15 mm, at the wavelength of the helium-neon laser $\lambda = 633$ nm (and at the wavelength $\lambda = 750$ nm of a laser diode), an effective refractive index change of only $\Delta N = 4 \cdot 10^{31}$ 5 (and of $\Delta N = 5 \cdot 10^{-5}$, respectively) will cause a phase change of $\Delta\Phi = 2\pi$. Depending on the method employed for measuring the phase difference, phase changes $\Delta\Phi(t)$ can be measured with a resolution of $\delta(\Delta\Phi) = \pi$ to $\delta(\Delta\Phi) = 2\pi/100$ and even to $\delta(\Delta\Phi) = 2\pi/1000$. Therefore, in the mentioned example changes in the effective refractive index $\Delta N$ of $\delta(\Delta N) = 2 \cdot 10^{-5}$ to $\delta(\Delta N) = 4 \cdot 10^{-7}$, and even to $\delta(\Delta N) = 4 \cdot 10^{-8}$ can be resolved.

The effective refractive index N depends on the refractive index of the medium covering the waveguide and on the thickness of an adlayer adsorbed on the surface of the waveguiding film or strip. Changes in $\Delta N(t)$ and, consequently, in the phase difference $\Delta\Phi(t)$ arise, if A) the refractive index of the medium covering the measuring section of the waveguiding film or strip changes, or B) substances, i.e., molecules, atoms, or ions are a) deposited on the measuring section of the waveguiding film or strip by unspecific adsorption, chemisorption or binding, i.e., if an adsorbed adlayer is formed, or b) if the waveguiding film or strip is micoporous, are deposited or adsorb in these micropores.

Therefore, with the method according to the present invention the following three measurements can be performed:

1. changes in refractive index of the sample can be measured, in particular for liquid samples. The method according to the present invention is suited for being used as a differential refractometer.

2. the adsorption of substances out of a gaseous or liquid sample can be measured. The method according to the present invention is so sensitive that sub-monomolecular layers of adsorbed molecules can be detected.

Examples for this are: with waveguiding films of $SiO_2$-$TiO_2$, changes in relative humidity, for instance of the relative humidity of air, can be measured, as water is adsorbed on the surface and is sorbed in the micropores of the $SiO_2$-$TiO_2$ film. The method according to the present invention is suitable as a humidity sensor.

3. specific substances in the sample can be detected selectively. For that purpose a chemo-responsive layer on the surface of the measuring section is required that selectively adsorbs, chemisorbs, or binds the substance to be detected, and thus either changes its refractive index or thickness, or effects the deposition of an adlayer on the chemo-responsive layer. This chemo-responsive layer can also be provided in the micropores of a porous waveguide. A semi-permeable membrane can also be provided in front of the chemo-responsive layer so that only those substances in the sample which diffuse through said membrane can interact with the chemo-responsive layer.

Examples of chemo-responsive layers are the following:

a) the chemo-responsive layer consists of a, for example, monomolecular layer of molecules of an antibody, which are bound, preferably covalently bound, to the waveguiding film or strip. If the antigen or hapten corresponding to that antibody is present in the sample, the antigen or hapten molecules bind to the antibody molecules and thus form an adlayer, the formation of which is detected with the method according to the present invention. The immuno-reaction between the antigen or hapten and the corresponding antibody is highly specific and selective, in particular if monoclonal antibodies are used. Analogously, if the measuring section is coated with antigen or anti-antibody molecules, to those immobilized molecules the corresponding antibody molecules in the sample will bind.

From the literature techniques for production of monoclonal antibodies (MAB's) are known; MAB's against numerous antigens such as bacteria, fungi, viruses, or fragments thereof, and haptens, for example, hormones or toxic substances, have been produced. Therefore the method according to the present invention can be applied in medical diagnostics for the detection of antibodies and antigens in body fluids, in agrodiagnostics for the detection of plant diseases, in the food industry for the detection of bacterial contaminations, and for the detection of toxic substances. Methods for covalent immobilization of antibodies to surfaces, for example to glas and $SiO_2$-surfaces, have been described in the literature.

b) From the literature [A. Kindlund and I. Lundström, Sensors and Actuators 3,63–77 (1982/83); M. S. Nieuwenhuizen and A. W. Barends, Sensors and Actuators 11,45–62 (1987); Liedberg, Nylander, and Lundström, Sensors and Actuators 4,229–304 (1983)] compounds are known, that selectively bind or absorb certain gases and thereby change their refractive index. Examples for this are silicon oils which absorb halogenated hydrocarbons. If those substances are used as chemo-responsive layers, with the method according to the present invention gases, for example, toxic or dangerous gases, can be detected very sensitively.

For the detection of hydrogen, palladium can be deposited on the surface or in the pores of the waveguiding film.

c) With an organophilic chemo-responsive layer, which absorbs or binds hydrocarbons, contaminations such as oil, or Diesel fuel can be detected in water. From the literature [F. K. Kawakara and R. A. Fiutem, Analytica Chimica Acta 151,315 (1983)] it is known that silanes have this organophilic property.

d) The measurement of the concentrations of ions, for example, of $H^+$- ions (pH-value) or $K^+$-ions, is possible with suitable chemo-responsive layers. Suited for the measurement of pH-values are chemo-responsive layers consisting of indicator dyes, chemisorbed or bound, or embedded in a polymer. Since indicator dyes change their colour with pH-value, they must change their refractive index in wavelength ranges where they exhibit low light absorption, which is a well-known fact following from the dispersion relations. Suitable for the measurement of $K^+$-ion concentrations is a chemo-responsive layer consisting, for example, of valinomycin molecules embedded in a polymer, which very selectively bind $K^+$-ions.

The dependence of the sensitivity of the method according to the present invention on the properties of the employed waveguide is considered in the following for the case of a planar waveguide and the use of the $TE_0$-mode and the $TM_o$-mode. The sensitivity is proportional to the temporal change of the difference $\Delta N(t) = \Delta N(t;TE_0) - N(t;TM_0)$ of the effective refractive indices of the two modes, which is induced by the sample. The effective refractive index changes $\Delta N(t;TE_0)$ and $N(t;TM_0)$ of the two modes themselves are great, if said modes interact strongly with the sample and with the chemo-responsive layer changed by the sample, respectively. This is the case, if their field is spatially strongly concentrated, i.e., if the effective film thickness $d_{eff}$ is as small as possible. The effective film thickness $d_{eff}$ is defined as the sum of the geometrical thickness d of the waveguiding film and the penetration depths of the evanescent fields into the substrate on the one side and into the sample and/or the chemo-responsive layer and the sample on the other side. The thickness $d_{eff}$ is small if d is small and if the difference $n_1 - n_2$ of the refractive indices of waveguiding film ($n_1$) and substrate ($n_2$) is as great as possible, preferably is $n_1 - n_2 > 0.25$. The film thickness d has to be chosen greater than the cut-off-thickness $d_c(TM_0)$ of the $TM_0$-mode, so that both the $TE_0$- and the $TM_0$-modes can propagate in the waveguide. The range of thicknesses d, in which the sensitivity of the method according to the present invention is high, can be determined without difficulty by the man of the art by simple calculations or a suitable series of experiments in the given case; said range is dependent on the refractive indices $n_1$ and $n_2$ and that ($n_4$) of the sample, and of the refractive indices and thicknesses of the chemo-responsive layer an an adsorbed adlayer. It is advantageous, to choose the thickness d—at least at the measuring section—to be smaller than the cutoff-thickness $d_c(TE_1)$ of the $TE_1$-mode, so that the guided wave can propagate only as the $TE_0$-mode and the $TM_0$-mode, and that no modes of higher order $m > 1$ can propagate and potentially can cause disturbances. For waveguiding films of $SiO_2$ and $TiO_2$ with $n_1 \approx 1.75$ on Pyrex glas substrates with $n_2 \approx 1.47$, the ranges of high sensitivity were found to be: a) in gaseous samples (where $n_4 \approx 1$) 220 nm < d < 420 nm and b) 150 nm < d < 390 nm in aqueous samples (where $n_4 \approx 1.33$), for the measurement of refractive index changes of the sample and of the adsorption of proteins on the waveguide surface. The given values for the lower bound of d correspond to about 5/3 of the cutoff thickness $d_c(TM_0)$ of the $TM_0$-mode.

The waveguiding films or strips are preferably made of materials with a high index of refraction $n_1$, for example, of mixtures of $SiO_2$ and $TiO_2$ ($n_1 \approx 1.75$) or of $Si_3N_4$ ($n_1 \approx 2.0$) on substrates with much smaller refractive index $n_2$, made preferably of glas ($n_1 < 1.5$) for example, of Pyrex glas. As substrate also a silicon wafer can be used, if the surface of which has been coated with a buffer layer that does not absorb light, preferably consisting of $SiO_2$, to avoid any attenuation of the guided wave. The waveguiding films or strips can also be fabricated of polyimid ($n_1 \approx 1.8$) on substrates made of glas or polymer, preferably polymethylmethacrylate (PMMA) or polycarbonate. Films of mixtures of $SiO_2$ and $TiO_2$ can, for example, be fabricated by dip-coating from organo-metallic solutions by the sol-gel process; films of $Si_3N_4$ by a CVD process.

The present invention is described below, by way of examples in the appended drawings.

DESCRIPTION OF THE INVENTION

Figure 1:
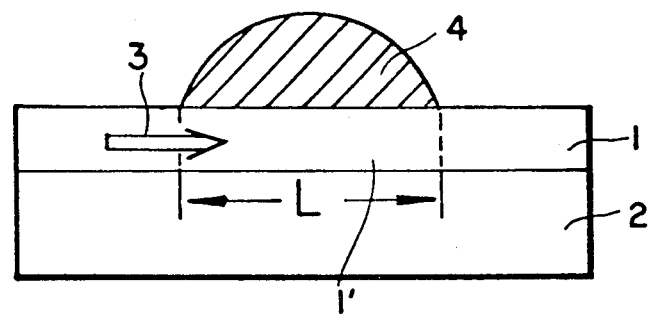
FIG. 1 a schematic longitudinal sectional view through a planar waveguide with the measuring section and the sample, FIG. 2 a schematic longitudinal sectional view through a planar waveguide with the measuring section and a reflector, FIG. 3 a schematic cross-sectional view through a strip waveguide on a planar substrate, FIG. 4 a schematic cross-sectional view through a strip waveguide on a cylindrical substrate, FIG. 5 a schematic representation of an apparatus in accordance with the present invention in longitudinal sectional view through a waveguide, FIG. 6 a schematic representation of an apparatus in accordance with the present invention in longitudinal sectional view through a waveguide whereby the guided mode interacts twice with the sample, FIG. 7 a schematic longitudinal sectional view through a planar waveguide which has a a smaller thickness at the measuring section than outside of said measuring section, FIG. 8 a schematic longitudinal sectional view through the waveguide, which outside the measuring section is coated with a protective layer and which at the measuring section is coated with a chemo-responsive layer, and where between waveguide and substrate a heating layer and above the measuring section a cell are provided, FIG. 9 a schematic perspective representation of the part of the apparatus according to the present invention for the measurement of the phase difference $\Delta\Phi(t)$ in a single measurement channel, FIG. 10 a schematic representation of the part of the apparatus according to the present invention for the measurement of the phase difference $\Delta\Phi(t)$ with a Wollaston prism for division of the outcoupled light into two measurement channels, FIG. 11 a schematic representation of the part of the apparatus according to the present invention for the measurement of the phase difference $\Delta\Phi(t)$ with a beam splitter and two Wollaston prisms for division of the outcoupled light into four measurement channels.

FIG. 1 shows a planar waveguide which consists of a waveguiding film 1 on the substrate 2. The guided wave 3 consists of two coherently excited, mutually orthogonally polarized modes, a TE-mode and a TM-mode, preferably the $TE_0$-mode and the $TM_0$-mode. The incoupling of the wave 3 into the waveguide 1/2 is not shown. The guided wave 3 interacts with the sample 4 in a section 1' of length L of waveguide 1, which in the following is called measuring section. Also not shown is the outcoupling of the guided wave 3 out of the waveguide 1/2.

Figure 2:
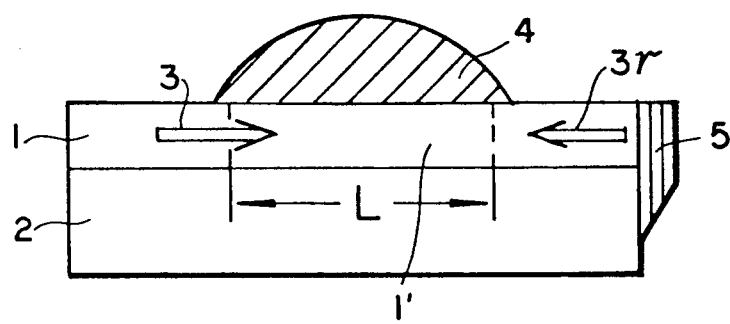

FIG. 2 shows a planar waveguide 1/2 with a reflector 5. The incoupled guided wave 3 interacts at the measuring section 1' with the sample 4 and is thereafter reflected by the reflector 5. The reflected wave 3r interacts also with the sample 4. In FIG. 2 neither the incoupling of the guided wave 3 nor the outcoupling of the guided wave 3r are shown. The sharply cut, broken, or polished end face of the waveguide, which preferably can be coated with a metal or dielectric mirror coating, can serve as the reflector 5. Not shown is that also a grating, for example, a surface relief grating on the waveguide 1/2 can serve as a reflector, if the Bragg condition is satisfied.

Figure 3:
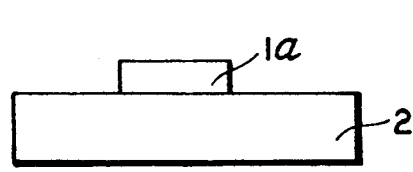

FIG. 3 shows a waveguiding strip 1a on a planar substrate 2. The width of the strip can typically be a few micrometers to a few millimeters. In the cross-sectional view not shown is the sample 4, which is applied to the measuring section 1' of length L. Not shown is the possibility to provide several strip waveguides parallel to each other on the same substrate 2. The substrates are typically 0.1 to 1 mm in thickness. Their sizes can vary within wide limits. Typically they are a few mm to 75 mm long, and a few mm to 25 mm wide.

Figure 4:
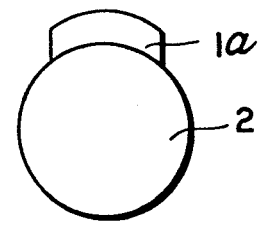

FIG. 4 shows the cross-sectional view through a waveguiding strip 1a on a cylindrical substrate 2. The diameter of the substrate 2 can typically be 0.1 mm to 10 mm, its length typically a few mm to 100 mm. With a reflector 5 at the end, this waveguide 1a/2 is particularly suited for dipping or insertion into a sample (not shown). The width of the waveguiding strip 1a can typically be between about 10 μm and a few mm. But it is also possible to choose its width equal to the circumference of the substrate 2, i.e., to coat the whole surface of the substrate 2 with a waveguiding film.

Figure 5:
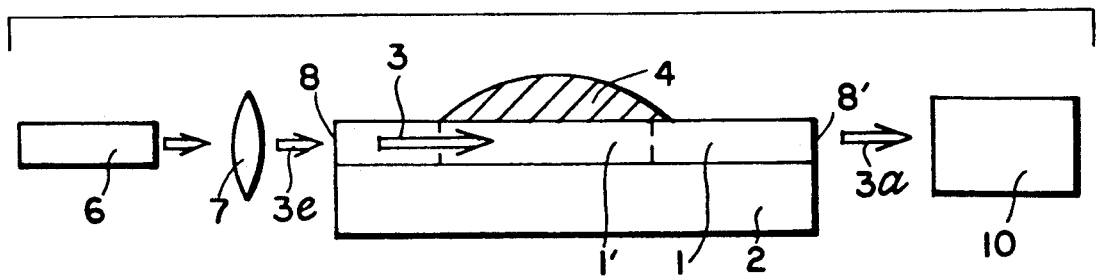

In the method according to the present invention as schematically shown in FIG. 5, polarized light emitted from a laser 6, preferably a helium-neon laser or a semiconductor laser, is focused with a system of spherical or cylindrical lenses 7, for example by a microscope objective lens, on the front face 8 of the planar waveguide 1/2 and is incoupled in such a way that the incoupled guided wave 3 consists of two mutually coherent and orthogonally polarized modes, preferably the $TE_0$-mode and the $TM_0$-mode, interacts with the sample 4 at the measuring section 1', and is coupled out of the waveguide 1/2 through the end face 8'. The time dependent phase difference $\Delta\Phi(t)$ between the two orthogonal polarization components s and p in the outcoupled light 3a is measured with a device 10. The advantage of cylindrical as compared to spherical lenses 7 is that the light is focused by the cylindrical lens only in the plane of projection of FIG. 5, i.e., on the front face of the waveguiding film 1, but not in the plane perpendicular to said plane of projection. A spherical lens 7 focuses the light also in the plane of the waveguiding film 1 and thus causes a divergence of the incoupled guided wave 3, which may be disadvantageous. If a laser emitting unpolarized light is employed, a polarizer is inserted between the laser and the lens 7. The light incident onto the waveguide 1/2 is preferably at first polarized under an angle $\psi \approx 45°$ with respect to the plane of projection, so that the TE and the TM-modes are excited with about equal intensities. The outcoupled light 3a contains two orthogonal polarization components s and p which are linearly polarized perpendicular (s) and parallel (p) with respect to the plane of projection, and which correspond to the outcoupled TE- and TM-modes, respectively. The angle $\psi$ is preferably so re-adjusted, that the polarization components s and p in the outcoupled light 3a are of equal intensity and that consequently the interference fringes are of maximum modulation. In the device 10, which comprises polarization optical components, photodetectors, and electronic components for data logging, processing, and storage, the polarization coponents s and p are superimposed so that they can interfere with each other. The resulting intensities $I_j(t)$ are measured either in a single or in several measurement channels j=1,2, ... M, where M=1,2,3 or 4. From the intensities $I_j(t)$, which depend cosinusoidally on the phase difference $\Delta\Phi(t)$, said phase difference $\Delta\Phi(t)$ is determined as a function of time t. This is explained in more detail below with FIGS. 9-11.

Figure 6:
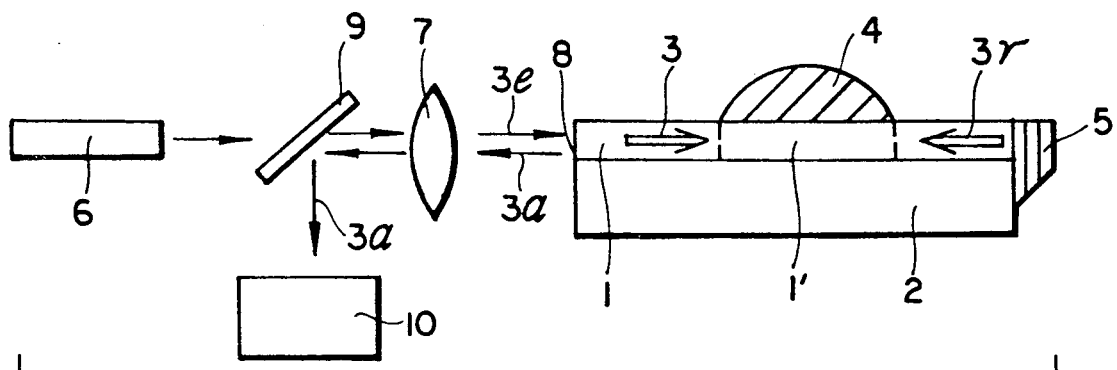

In the method in accordance with the present invention as schematically shown in FIG. 6, the guided wave 3 is produced as in the method shown in FIG. 5. After interaction with the sample 4 at the measuring section 1', the guided wave 3 is reflected by a reflector 5; the reflected wave 3r also interacts with the sample 4 at the measuring section 1', and thereafter is outcoupled through the same front face 8 through which the light was coupled into the waveguide 1/2. With a beam splitter 9 the outcoupled light 3a is separated spatially from the incident light 3e and is thereafter lead to the device 10 measuring the phase difference $\Delta\Phi(t)$. Advantages of this method are that the waveguide 1/2 can be directly inserted into a sample and that because of the double interaction with the sample 4 the sensitivity is twice as high. The waveguide 1/2 shown schematically in a longitudinal sectional view in FIGS. 5 and 6 can also be a strip waveguide 1a/2; in this case the method in accordance with the present invention functions in an analogous way.

Not shown are the possibilities to guide the incident laser light 3e and the outcoupled light 3a with fibre waveguides, in particular with polarization preserving monomode fibre waveguides, from the laser 6 to the planar waveguide 1/2 or to the strip waveguide 1a/2, and/or from said waveguides to the device 10. The fibres can, for example, be directly attached to the front and end faces 8 and 8' of the planar waveguide 1/2 or of the strip waveguides 1a/2.

Also not shown is the possibility to couple light into the waveguide 1/2 or 1a/2 and/or out of said waveguides with prism, grating, or taper couplers.

Figure 7:
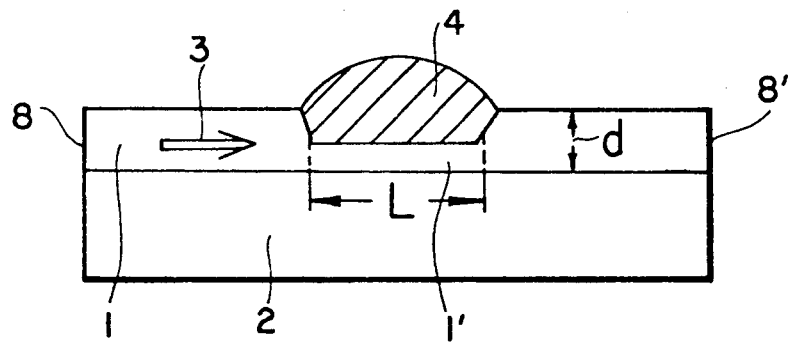

FIG. 7 shows a planar waveguiding film 1, which at the measuring section 1' has a smaller film thickness d than outside said section 1', in particular in the regions of the front and end faces 8 and 8'. The advantages of this apparatus according to the present invention are: 1. For the incoupling of the laser light 3e into the waveguide 1/2 through the front face 8 a greater film thickness is advantageous, because the adjustment of the lenses 7 is easier and the incoupling efficiency is higher, and 2. the method according to the present invention has a higher sensitivity if the film thickness d is small in the region of the measuring section 1', what already has been described above. In an analogous way this also holds for waveguiding strips 1a/2.

Figure 8:
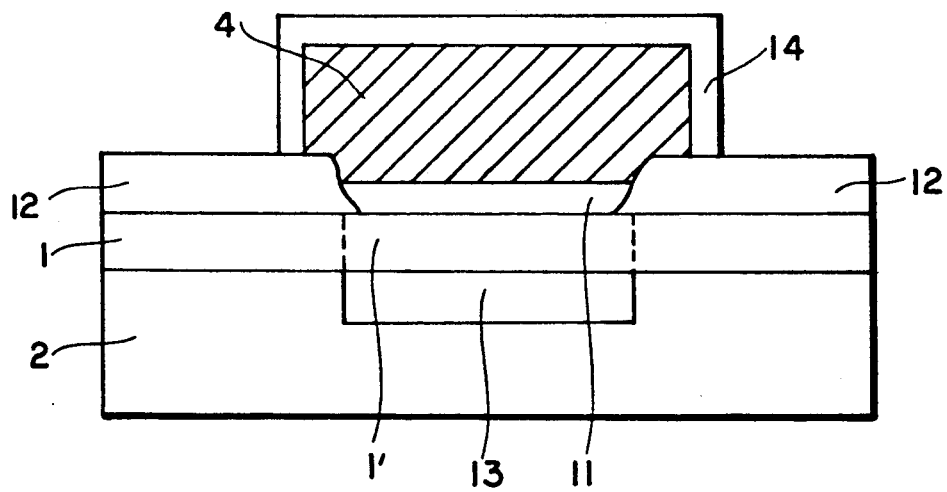

FIG. 8 shows a protection layer 12 with which the waveguiding film 1 is covered everywhere with the exception of the measuring section 1', in order to prevent any undesired interaction of the guided wave with the environment. The protection layer 12 has to have a refractive index $n_{12}$ which is smaller than the refractive index of the waveguiding film 1 or strip 1a and also smaller than the effective refractive indices N of the two modes of the guided Wave 3. The thickness of the protection layer 12 has to be greater than the penetration depths $(\lambda/2\pi)[N^2 - n_{12}^2]^{-\frac{1}{2}}$ of the evanescent wave of the fields of the guided wave 3 in the protection layer 12. Suitable materials for the protection layer 12 are preferably $SiO_2$, glas resin polymers, or polymers such as PMMA or polycarbonate, which, for example, can be applied by spin coating or dip coating. At the measuring section 1' the waveguiding film 1 can be covered with a chemo-responsive layer 11. Between the substrate 2 and the waveguiding film 1 a heating layer 13, for example an indium-tin-oxide (ITO) layer, can be provided at least in the region of the measuring section 1'. By an electric current the heating layer 13 can be heated; the resulting increase in temperature effects the desorption of adsorbed molecules in particular in gaseous samples, and the measuring section 1' can thus be cleaned from adsorbates. The sample 4 is applied to the measuring section 1'. The measuring section 1' can also be covered with a cell 14, into which the sample is filled. The walls of the cell 14 are preferably attached to the protection layer 12.

Figure 9:
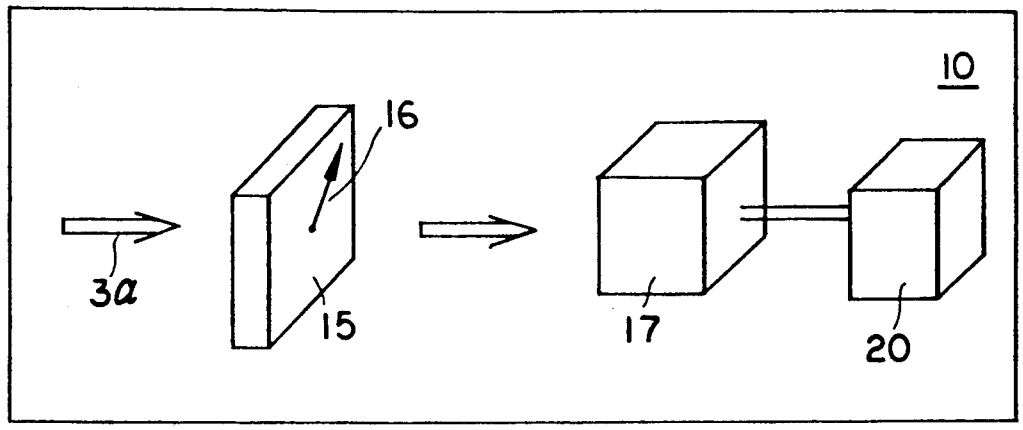
Figure 10:
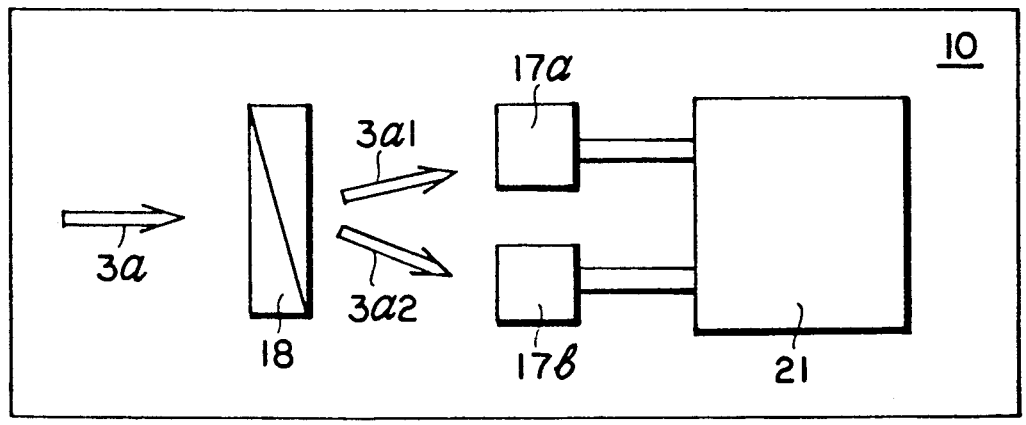
Figure 11:
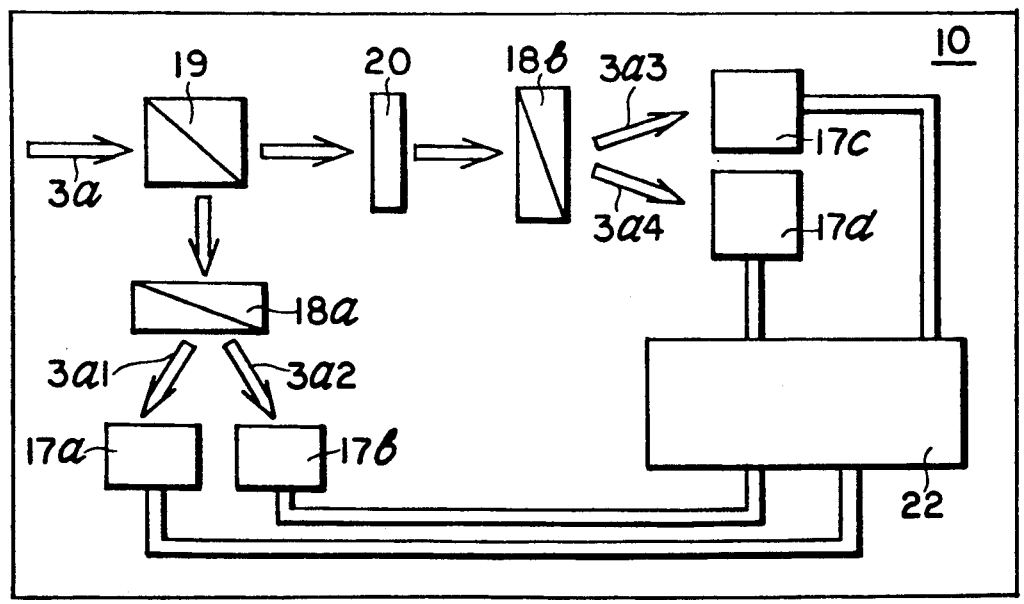

FIGS. 9-11 show examples of the part 10 of the apparatus according to the present invention that is used for measuring the phase difference $\Delta\Phi(t)$ between the polarization components s and p of the outcoupled light 3a. FIG. 9 shows an embodiment with a single measurement channel. The outcoupled light 3a falls through a polarizer 15, the transmission direction 16 of which is orientated to coincide with the bisector between the polarization directions of the components s and p, onto the photodetector 17 measuring the intensity I(t), which is recorded, processed, and evaluated by the electronics 20. From Eq. 6 it follows that the temporal changes of the phase difference $\Delta\Phi(t)$ can be determined from I(t), for example, by counting the maxima and minima of I(t).

FIGS. 10 and 11 show embodiments of the apparatus for measuring the phase difference $\Delta\Phi(t)$ with several measurement channels. The outcoupled light is divided with beam splitters, and/or Wollaston prisms, into M measurement channels. Between the polarization components s and p different additional phase differences $(\Phi_0)_j$ in the measurement channels $j=1,2, \ldots M$ are produced by polarization optical components such as Wollaston prisms, phase retardation plates, for example $\lambda/4$ plates; and with the Wollaston prisms or with polarizers said two polarization components s and p are superimposed so that they can interfere with each other. The resulting intensity $$I = I_s + I_p + 2(I_s I_p)^{\frac{1}{2}} \cos[\Delta\Phi + \Delta\Phi(t) + (\Phi_0)_j] \quad (7)$$

is measured by a photodetector. Here $I_s$ and $I_p$ are the intensities that the polarization components s and p would produce separately, $\Delta\Phi$ is the constant phase difference, and $\Delta\Phi(t)$ the time dependent phase difference.

The longitudinal sectional views shown in FIGS. 10 and 11 are with respect to the longitudinal sectionals views shown in FIGS. 5 and 6 rotated by 45° about the optical axis of the outcoupled light. FIG. 10 shows a device 10 with two measurement channels (M=2). The outcoupled light 3a is divided by the Wollaston prism 18 into two orthogonally polarized components 3a1 and 3a2, which fall onto the photodetectors 17a and 17b. In the two measurement channels $j=1$ and $j=2$ the polarization components s and p are superimposed and interfere with the phase differences $(\Phi_0)_1 = 0$ and $(\Phi_0)_2 = \pi$, respectively. From Eq. (7) it follows that the difference of the intensities $I_1(t) - I_2(t)$ is proportional to $\cos[\Delta\Phi + \Delta\Phi(t)]$, this difference signal is formed, processed, and evaluated by the electronics 21, for example, by counting of the zero crossings.

FIG. 11 shows a device 10 with four measurement channels (M=4). The outcoupled light 3a is divided into two beams by a beam splitter 19. Each of said beams are divided by the Wollaston prisms 18a and 18b into two orthogonally polarized beams so that four beams 3a1-3a4 are produced. In front of the Wollaston prism 16b, a $\lambda/4$-plate 20 is inserted, which produces a phase difference of $\pi/2$ between the polarization components s and p. In the four measurement channels 1-4 the polarization components s and p interfere with the following values of the phase difference $\Phi_0$; viz. $(\Phi_0)_1 = 0$, $(\Phi_0)_2 = \pi$, $(\Phi_0)_3 = \pi/2$, and $(\Phi_0)_4 = 3\pi/2$. From Eq. (7) it follows that the difference $I_1(t) - I_2(t)$ is proportional to $\cos[\Delta\Phi + \Delta\Phi(t)]$, and the difference $I_4(t) - I_3(t)$ is proportional to $\sin[\Delta\Phi + \Delta\Phi(t)]$. In the electronics 22 said differences and the ratio $[I_4(t) - I_3(t)]/[I_1(t) - I_2(t)] = \tan[\Delta\Phi + \Delta\Phi(t)]$ are formed, from which the phase difference $\Delta\Phi(t)$ is determined. The phase difference $\Delta\Phi(t)$ can be determined with a resolution of $\delta(\Delta\Phi) = 2\pi/100$.

Not shown is the possibility to divide the outcoupled light 3a into three measurement channels (M=3), to superimpose the polarization components s and p so that they can interfere in the measurement channel j with the additional phase differences $(\Phi_0)_j$, viz., $(\Phi_0)_1 = 0$, $(\Phi_0)_2 = 2\pi/3$, and $(\Phi_0)_3 = 4\pi/3$, or alternatively $(\Phi_0)_1 = 0$, $(\Phi_0)_2 = \pi/2$, and $(\Phi_0)_3 = \pi$, and to measure the intensities $I_1(t)$, $I_2(t)$, and $I_3(t)$ with photodetectors and to electronically record and process said intensities and to determine from them the phase difference $\Delta\Phi + \Delta\Phi(t)$.

The following methods to determine the phase difference $\Delta\Phi(t)$ in a single measurement channel are not shown in figures; the devices correspond essentially to that in FIG. 9, however, they comprise additional components. a) In a "quasi-heterodyne-method", an additional time dependent phase difference $\Phi_0(t)$ between the polarization components s and p is produced, for example, with an electro- or elasto-optical modulator or by displacement of a Babinat compensator (these components are missing in FIG. 9 ; $\Phi_0(t)$ is varied in one period T in M=3 or M=4 discrete steps. In the example M=3, the values of $(\Phi_0)_1 = 0$, $(\Phi_0)_2 = 2\pi/3$, and $(\Phi_0)_3 = 4\pi/3$ are chosen in the 1.,2., and 3. third of the period T. From the tripel of the measured intensity values $I_1(t)$, $I_2(t)$, and $I_3(t)$ in the three time intervals the phase difference $\Delta\Phi(t)$ is determined from the following relation: $\Delta\Phi + \Delta\Phi(t) = \arctan\{\sqrt{3}[I_3(t) - I_2(t)]/[2I_1(t) - I_2(t) - I_3(t)]\}$, which can be derived from Eq.(7). In the example with M=4 the values of $(\Phi_0)_1 = 0$, $(\Phi_0)_2 = \pi$, $(\Phi_0)_3 = \pi/2$, and $(\Phi_0)_4 = 3\pi/2$ are chosen in the 1.,2.,3., and 4. fourth of the period T. From the quadrupel of intensity values $I_1(t)$, $I_2(t)$, $I_3(t)$, and $I_4(t)$ measured in the four time intervals the phase difference $\Delta\Phi(t)$ is determined from the following relation, which is derived from Eq.(7):

$$\Delta\Phi + \Delta\Phi(t) = \arctan\{[I_4(t) - I_3(t)]/[I_1(t) - I_2(t)]\}.$$

b. The phase difference $\Phi_0(t)$ is varied linearly between $-\pi$ and $+\pi$ periodically with period T, with the modulators described above in point a). It is determined at which value $\phi_0$, of $\Phi_0$ the measured intensity I(t) assumes its minimum value; according to Eq.(7) the phase difference is determined from: $\Delta\Phi + \Delta\Phi(t) = \pi - \Phi_0$, The methods a) and b) have a resolution of $\delta(\Delta\Phi) \leq 2\pi/100$.

c. The phase difference $\Delta\Phi(t)$ can also be measured with heterodyne interferometers. Thereby a frequency difference $\Delta\nu$ is generated between the polarization components of the laser light 3e incident on the waveguide 1/2, 1a/2, and thus between the two modes of orthogonal polarization of the guided wave 3. Said frequency difference $\Delta\nu$ can be generated, for example, in a helium-neon laser by a Zeeman splitting, with an acousto-optic modulator, or with a phase retardation $\lambda/2$-plate rotating with constant angular velocity and a stationary $\lambda/4$-plate. The intensity I(t) measured by the photodetector 17 oscillates with frequency $\Delta\nu$. Measured is the relative phase difference between this intensity I(t) and a reference intensity oscillating with the same frequency $\Delta\nu$, which is measured with a second photodetector. Said reference intensity is derived with a beam splitter from the laser light 3e incident on the waveguide 1/2,1a/2. Thus the phase difference $\Delta\Phi(t)$ can be measured with a resolution of $\delta(\Delta\Phi) \leq 2\pi/1000$.

While the foregoing description and drawings represent the preferred embodiments of the present invention, it will be obvious to those skilled in the art that various changes and modifications may be made therein without departing from the true spirit and scope of the present invention.

What is claimed is:

1. Integrated optical interference method in particular for the selective detection of substances in liquid, gaseous, or solid samples, and/or for the measurement of changes of the refractive indices of liquid and gaseous samples, and/or of ion concentrations, comprising the steps of: coupling polarized laser light into a thin optical planar waveguide or a thin strip waveguide in such a way, that two mutually coherent and orthogonally polarized modes are excited, which propagate in the waveguide as a guided wave together on the same path and which thereby interact at least once with the sample applied to the surface of the measuring section of the waveguide, that said guided wave is outcoupled out of the waveguide, and that the phase difference $\Delta\Phi(t)$ between the mutually orthogonal polarization components s and p of the outcoupled light, which are produced by the two orthogonally polarized modes, is measured as a function of time.

2. Method according to claim 1, wherein on the surface of the measuring section additionally a chemoresponsive layer (11) is provided, which chemically selectively binds, or adsorbs, or chemisorbs molecules, atoms, or ions from the sample to be analysed.

3. Method according to claim 1, wherein the incident polarized laser light is directly coupled into the waveguide through its front face and is outcoupled preferable through either the front face (8) or the end face.

4. Method according to claim 1, wherein the incident laser light is either linearly polarized under an angle $\psi\neq 0°$ and $\psi\neq 90°$, preferably under an angle $\psi\approx 45°$, with respect to the normal on the waveguide, or elliptically, preferably circularly, polarized, and is focused on the front face of the waveguide with one or several spherical or cylindrical lenses.

5. Method according to claim 1, wherein the incoupled wave in the waveguide after interaction with the sample is reflected by a reflector and after a second interaction with sample is outcoupled on the same side of the waveguide on which it was coupled in, and that the outcoupled light is separated spatially by a beam splitter from the incident laser light.

6. Method according to claim 1, wherein polarized laser light is coupled into a planar waveguide in such a way that the incoupled guided wave consists of a TE-mode and a TM-mode which are mutually coherently excited, preferably of the $TE_0$-mode and the $TM_0$-mode, and that the film thickness of the waveguiding film at the measuring section is preferably chosen greater than about 5/3 of the cut-off-thickness $d_c(TM_0)$ of the $TM_0$-mode and smaller than the cut-off-thickness $d_c(TE_1)$ of the $TE_1$-mode.

7. Method according to claim 1, wherein polarized laser light is coupled into a planar waveguide or a strip waveguide with a fibre waveguide, preferably with a polarization preserving monomode fibre waveguide, and/or that the outcoupled light is guided with a fibre waveguide, preferably with a polarization preserving monomode fibre waveguide, to the device measuring the phase difference $\Delta\Phi(t)$.

8. Method according to claim 1 wherein, the phase difference $\Delta\Phi(t)$ is determined as a function of time t, by effecting the superposition and interference of the polarization components s and p of the outcoupled light with a polarizer, whose transmission direction coincides with the bisector between the directions of polarization of said components s and p, by measuring the resulting intensity I(t) with a photodetector as a function of time t, and by electronically recording the changes of I(t), preferably by counting the maxima and minima of I(t).

9. Method according to claim 1, wherein characterized in that the phase difference $\Delta\Phi(t)$ is determined as a function of time t, by effecting with a Wollaston prism the superposition and interference of the polarization components s and p of the outcoupled light coupled out of the waveguide, whereby the outcoupled light is also divided into two beams, the intensities $I_1(t)$ and $I_2(t)$ of which are measured by two photodetectors, by electronically recording the intensities $I_1(t)$ and $I_2(t)$, and by further processing by counting the maxima, minima, and zero crossings of $I_1(t)-I_2(t)$.

10. Method according to claim 1, wherein the phase difference $\Delta\Phi(t)$ is determined as a function of time t, by dividing the outcoupled light coupled out of the waveguide with a beam splitter and two Wollaston prisms into four beams j=1,2,3, and 4, preferably of about equal intensities, whereby said Wollaston prisms effect the superposition and interference of the polarization components s and p in the four beams j=1-4 with the following constant phase differences $(\Phi_0)_j$, which are produced by said Wollaston prisms and a $\lambda/2$-plate, viz., $(\Phi_0)_1=0, (\Phi_0)_2=\pi, (\Phi_0)_3=\pi/2$, and $(\Phi_0)_4=3\pi/2$, by measuring the resulting intensities $I_1(t), I_2(t), I_3(t)$, and $I_4(t)$ in the four measurement channels with the photodetectors, and by electronically deriving the intensity differences $I_1(t)-I_2(t)$ and $I_4(t)-I_3(t)$ and the ratio $[I_4(t)-I_3(t)]/[I_1(t)-I_2(t)]$, which are further processed and evaluated with an algorithm.

11. Method according to claim 1, wherein the phase difference $\Delta\Phi(t)$ is determined continuously at equal time intervals T, by introducing between the polarization components s and p of the light coupled out of the waveguide subsequently in the 1., 2., and 3. third of each time interval T the additional phase differences $(\Phi_0)_j$, where j=1,2, and 3, preferably $(\Phi_0)_1=0$, $(\Phi_0)_2=\pi/2$, and $(\Phi_0)_3=3\pi/2$, or alternatively and $(\Phi_0)_1=0, (\Phi_0)_2=2\pi/3$, and $(\Phi_0)_3=4\pi/3$, which are produced, for example, with an electro-optic or elasto-optic modulator or by displacement of a Babinet compensator, by effecting with a polarizer, whose transmission direction coincides with the bisector between the polarization directions of said components s and p, the superposition and interference of said polarisation components s and p, by measuring the resulting intensity I(t) with a photodetector, and by electronically recording and further processing of the intensities $I_1(t), I_2(t)$, and $I_3(t)$ measured in the time intervals of duration T/3.

12. Method according to claim 1, wherein the phase difference $\Delta\Phi(t)$ is determined as a function of time t continuously at equal time intervals T, by introducing an additional time dependent phase difference $\Phi_0(t)$ between the polarization components s and p of the light coupled out of the waveguide, whereby $\Phi_0(t)$ is varied between $-\pi$ and $\pi$, preferably linearly with time, periodically with period T, by effecting with a polarizer, the transmission direction of which coincides with the direction of the bisector between the polarization directions of the components s and p, the superposition and interference of said components s and p of the outcoupled light, and by measuring the resulting intensity I(t) with a photodetector, by electronically recording the temporal behaviour of I(t) in particular the maxima and minima of I(t) during the period T and by further signal processing and evaluation, whereby this procedure is repeated periodically with period T.

13. Method according to claim 1, wherein the phase difference $\Delta\Phi(t)$ is measured with a heterodyne method.

14. Method according to claim 1, wherein the sample to be analysed is either applied to the measuring section, or is filled into a cell covering the measuring section, or that the part of the waveguide with the measuring section is inserted into the gaseous, liquid, or solid sample.

15. Apparatus for performing a method of integrated optical interference for the selective detection of substances in liquid, gaseous, or solid samples, and/or for the measurement of changes of the refractive indices of liquid and gaseous samples, and/or of ion concentrations, comprising the steps of: coupling polarized laser light into a thin optical planar waveguide or a thin strip waveguide in such a way, that two mutually coherent and orthogonally polarized modes are excited, which propagate in the waveguide as a guided wave together on the same path and which thereby interact at least once with the sample applied to the surface of the measuring section of the waveguide, that said guided wave is outcoupled out of the waveguide, and that the phase difference $\Delta\Phi(t)$ between the mutually orthogonal polarization components s and p of the outcoupled light, which are produced by the two orthogonally polarized modes, is measured as a function of time; said apparatus comprising A) a thin planar waveguide or a thin strip waveguide, in which at least two orthogonally polarized modes can propagate, whereby the substrate is preferably either planar or cylindrical, and B) preferably one or several spherical or cylindrical lenses in the path of the incident laser light, and/or fibre waveguides, preferably polarization preserving fibre waveguides, for the guidance of the incident laser light and/or the guidance of the outcoupled light, and C) polarization optical components—for example, polarizers, Wollaston prisms, and phase retardation plates—furthermore beam splitters, and photodetectors in the path of the outcoupled light for the measurement of the phase difference $\Delta\Phi(t)$ between the polarization components s and p.

16. Apparatus according to claim 15, wherein, at the waveguide a reflector for the reflection of the guided wave is provided, whereby the reflector consists, for example, of the sharply cut or polished end face of the waveguide, onto which preferably a metal or dielectric mirror coating is deposited.

17. Apparatus according to claim 15 or 16, wherein between the lens and the front face of the waveguide an immersion liquid, for example, water or oil, is provided.

18. Apparatus according to claim 15, wherein the waveguiding film, at least at the measuring section, is covered with a chemo-responsive layer and/or contains said layer in its pores, which selectively chemically binds and/or preferentially adsorbs or chemisorbs the substance to be detected in the sample, or which changes its refractive index with the ion concentration in the sample or by a chemical effect of the substance to be detected in the sample.

19. Apparatus according to claim 18, characterized in that the chemo-responsive layer is a layer of molecules of either A) an antigen or preferably monoclonal anti-antibody for the detection of the corresponding antibodies in the sample, or B) a preferably monoclonal antibody for the detection of the corresponding antigen or hapten in the sample, which are bound, preferably by covalent binding, to the waveguiding film or strip.

20. Apparatus according to claim 15, wherein the waveguiding film outside of the measuring section is covered with a protection layer, preferably of silicon dioxide, glas resin, or polymers, which prevents any undesirable perturbation of the guided wave by the environment.

21. Apparatus according to claim 15, wherein a heating layer is provided between the substrate and the waveguiding film, at least at the measuring section.

22. Apparatus according to claim 15, wherein the waveguiding films or strips consist of A) mixtures of silicon dioxide and titanium dioxide or of silicon nitride on substrates of glas, preferably Pyrex glas, or of silicon wafers with a non-absorptive buffer layer, preferably of silicon dioxide. or B) polymers, for example, polyimid, on substrates of glas or polymers, for example, of polymethylmethacrylate (PMMA) or polycarbonate.

23. Apparatus according to claim 15, wherein for achievement of a higher incoupling efficiency and for the simplification of the adjustment of the incident laser beam, the planar waveguiding film or strip outside of the measuring section have a greater film thickness than at the measuring section (1,) itself.

* * * * *